United States Patent [19]

Saumarez et al.

[11] Patent Number: 5,292,348
[45] Date of Patent: Mar. 8, 1994

[54] IMPLANTABLE CARDIOVERTER/DEFIBRILLATOR AND METHOD EMPLOYING CROSS-PHASE SPECTRUM ANALYSIS FOR ARRHYTHMIA DETECTION

[75] Inventors: Richard Saumarez, Old Coulsdon, England; Anthony Murphy, Leichhardt, Australia

[73] Assignee: Telectronics Pacing Systems, Inc., Englewood, Colo.

[21] Appl. No.: 867,835

[22] Filed: Apr. 13, 1992

[30] Foreign Application Priority Data

Jun. 14, 1991 [AU] Australia ............................ PK6714

[51] Int. Cl.⁵ .............................................. A61N 1/39
[52] U.S. Cl. .......................................... 607/5; 607/14
[58] Field of Search .................. 128/419 D, 419 PG; 607/5, 14

[56] References Cited

U.S. PATENT DOCUMENTS

| | | | |
|---|---|---|---|
| 4,202,340 | 5/1980 | Langer et al. ................ | 128/419 D |
| 4,408,284 | 10/1983 | Kijesky et al. ................ | 364/485 |
| 4,475,551 | 10/1984 | Langer et al. ................ | 128/419 D |
| 4,790,317 | 12/1988 | Davies .......................... | 128/419 D |
| 4,875,483 | 10/1989 | Vollman et al. ............. | 128/419 PG |
| 4,901,082 | 2/1990 | Schreiber et al. ............ | 342/89 |
| 4,905,708 | 3/1990 | Davies .......................... | 128/705 |
| 4,982,375 | 1/1991 | Ng ................................. | 367/135 |
| 5,107,850 | 4/1992 | Olive ............................ | 128/419 D X |

FOREIGN PATENT DOCUMENTS

| | | | |
|---|---|---|---|
| 0253505 | 1/1988 | European Pat. Off. ...... | A61N 1/365 |
| 2109179 | 10/1971 | Fed. Rep. of Germany ......... | G01R 29/02 |

OTHER PUBLICATIONS

G. D. Bergland, "A Guided Tour of the Fast Fourier Transform", *IEEE Spectrum*, vol. 6, pp. 41–52, Jul. 1969.

*Primary Examiner*—Kee S. Cohen
*Assistant Examiner*—Jeffrey R. Jastrzab
*Attorney, Agent, or Firm*—Gottlieb, Rackman & Reisman

[57] ABSTRACT

A method and apparatus for detecting and reverting pathological heart rhythms of a patient are disclosed. A plurality of electrical heart rhythm signals of the patient are sensed at two different locations within the heart. The cross-phase spectra of the sensed heart rhythm signals for each heartbeat are calculated and such heart rhythms are classified based upon the information contained in the cross-phase spectra. Appropriate therapy is then delivered to the patient's heart to revert those of the heart rhythms that are classified as pathological.

17 Claims, 11 Drawing Sheets

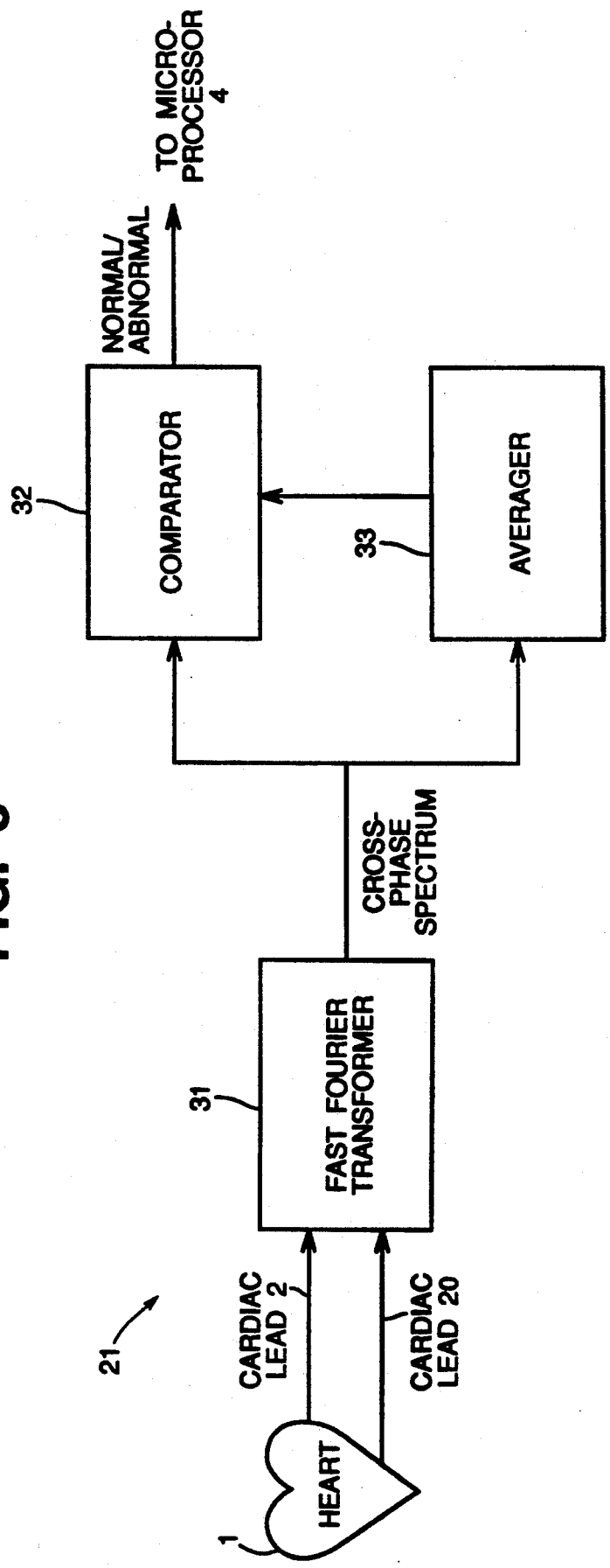

IMPLANTABLE CARDIOVERTER/DEFIBRILLATOR AND METHOD EMPLOYING CROSS-PHASE SPECTRUM ANALYSIS FOR ARRHYTHMIA DETECTION

TECHNICAL FIELD

This invention relates to implantable medical devices which monitor a patient's cardiac state for the presence of arrhythmias, and which deliver therapy in an attempt to revert detected arrhythmias and restore a normal sinus rhythm to the patient. In particular it relates to an apparatus and method for arrhythmia detection which employs cross-phase spectrum analysis.

PRIOR ART

Current antitachycardia devices attempt to discriminate physiological from pathological cardiac rhythms based on the sensed heart rate. U.S. Pat. No. 4,875,483 to W. Vollman et al. discloses such a device. Sudden onsets of high rate, rate stability, and sustained high rate have also been utilized in current devices to provide some discrimination between different rhythms of similar rate, as is disclosed in European Patent Publication No. 253,505.

Other techniques have been proposed which take into consideration the timing relationship between two different electrodes (see, e.g., U.S. Pat. No. 4,905,708 to D. W. Davies), or the morphology of the ventricular depolarization waveform (see, e.g., U.S. Pat. No. 4,905,708 to D. W. Davies and U.S. Pat. No. 4,475,551 to Langer et al.). Also, in German patent (DE) No. 2,109,179, the spectrum of the ventricular signal has also been considered in order to identify extrasystoles in the electrocardiogram. Techniques which are based on rate parameters are unable to distinguish between physiological and pathological rhythms that have the same rate. An important example of this is sinus tachycardia (a physiological rhythm) and slow ventricular tachycardia (a pathological rhythm.)

Furthermore, these prior art techniques are incapable of discriminating between different types of pathological tachycardia, which may be amenable to different types of therapy. An example of this is atrial fibrillation and slow ventricular tachycardia.

Detection methods which are based on timing relationships at two different sites are subject to problems associated with cross-channel blanking, far-field sensing, and timing jitter.

Techniques based on signal morphology are unreliable because they need a template for normal morphology. The morphology of a physiological rhythm may change with time, disease state, circulating catecholamines, or other factors. Thus it is difficult to determine whether variation from the template morphology is due to a pathological rhythm, or due to changes in the physiological rhythm. Adaptive techniques to account for such variations are very difficult to administer.

The cross-spectrum has been used by a number of investigators for various purposes. The real and imaginary parts of the cross-spectrum have been used in radar to deconvolve the channel spectrum, leaving a noise free version of the echo signal (see, e.g., U.S. Pat. No. 4,901,082 to Schreiber et al.). The magnitude of the cross-spectrum has been used in seismic analysis to estimate the spectra of the sources. The cross-spectral signal density has been used to estimate acoustic energy distribution and propagation of noise sources. (See, e.g., U.S. Pat. No. 4,982,375 to K. W. Ng.)

The phase relationship between two signals has been used to determine wavefront vector coordinates in radio wave interferometry. The phases in this case are compared by simple subtraction, not via the phase of the cross-spectrum.

The phase component of the spectrum of a single signal has been used to detect sinusoidal waveforms corrupted by noise (see e.g., U.S. Pat. No. 4,408,284 to Kijesky et).

None of these patents propose, as in the case of the present invention, to consider the phase component of the cross-spectrum. In particular, the present invention proposes to look at the cross-phase spectrum generated from ventricular intracardiac signals, and to use this information to identify differing cardiac rhythms.

The cross-spectrum is a complex-valued function that is defined for two real valued signals as the product of the Fourier Transform of the first signal with the complex conjugate of the Fourier Transform of the second signal. For two signals s(n) and t(n) defined for values of the discrete parameter n, it is appropriate to utilize discrete Fourier Transforms:

$$T(k) = \sum_{n=0}^{N-1} t(n)e^{-j(2\pi/N)nk}$$

$$S(k) = \sum_{n=0}^{N-1} s(n)e^{-j(2\pi/N)nk}$$

where k=0, 1, ..., N−1.

The cross-spectrum of the two signals is then defined as:

$$C(k) = T(k)S^*(k)$$

where * denotes complex conjugation.

Considered as a complex number C(k) has a magnitude component $|C(k)|$ and a phase component $\angle C(k)$ such that $$C(k) = |C(k)|e^{j\angle C(k)}$$

where k=0, 1, ..., N−1 The phase component $\angle C(k)$ is known as the cross-phase spectrum.

OBJECTS OF THE INVENTION

It is an object of this invention to reliably differentiate in patients between psysiological heart rhythms and pathological heart rhythms It is a further object of the invention to discriminate between these two types of rhythms even when the possible ranges of heart rates for physiological or pathological tachycardias have a degree of overlap.

It is another object of the invention to adapt to the normal changes in electrogram morphology, so that the discrimination is unaffected by these changes.

It is a still further object of the invention to correctly determine when it is appropriate to withhold therapy in response to a physiological rhythm with high ventricular rate, based on the improved classification of heart rhythm.

It is yet another object of the invention to sub-classify between different types of pathological heart rhythms, for example atrial fibrillation (AF) and slow ventricular tachycardia (VT).

It is a further object of the invention to select more appropriate therapy modalities, based on this sub-classification of pathological heart rhythms.

Further objects and advantages of the invention will become apparent as the following description proceeds.

SUMMARY OF THE INVENTION

Briefly stated, and in accordance with one embodiment of the invention, there are provided an apparatus and method capable of differentiating between physiological and pathological heart rhythms. The apparatus provides two bipolar sensing electrodes, for registering the electrogram from two different sites within the heart. There is further included a signal processing element for calculating the cross-phase spectrum of the two electrograms. There is also included in the apparatus a classification device which classifies the heart rhythm based upon the information contained in the cross-phase spectrum.

The bipolar sensing electrodes may be on separate leads, or on one lead only. An individual electrode may be used for dual purposes so that electrode pairs can be obtained using three electrodes in total.

BRIEF DESCRIPTION OF THE DRAWINGS

FIG. 3 depicts a block diagram of the module for cross-phase spectrum calculation and rhythm classification of FIG. 2;

BEST MODE OF THE INVENTION

The term "therapy", as used herein, includes the processes used between the detection and reversion of an arrhythmia, and includes the actions of antitachycardia pacing, bradycardia pacing, cardioversion shock, defibrillation shock, and the actions of drugs. The term "cardioversion" refers to the discharge of electrical energy onto the cardiac tissue in an attempt to terminate or revert a tachycardia. It may range from a high (up to 40 Joules or more) to a low (less than 1 Joule) of energy discharge. The discharge may be monophasic or biphasic but is not restricted to these waveforms. Cardioversion shocks may or may not be synchronized to the rhythm of the heart. Defibrillation is a particular example of cardioversion.

Figure 1:
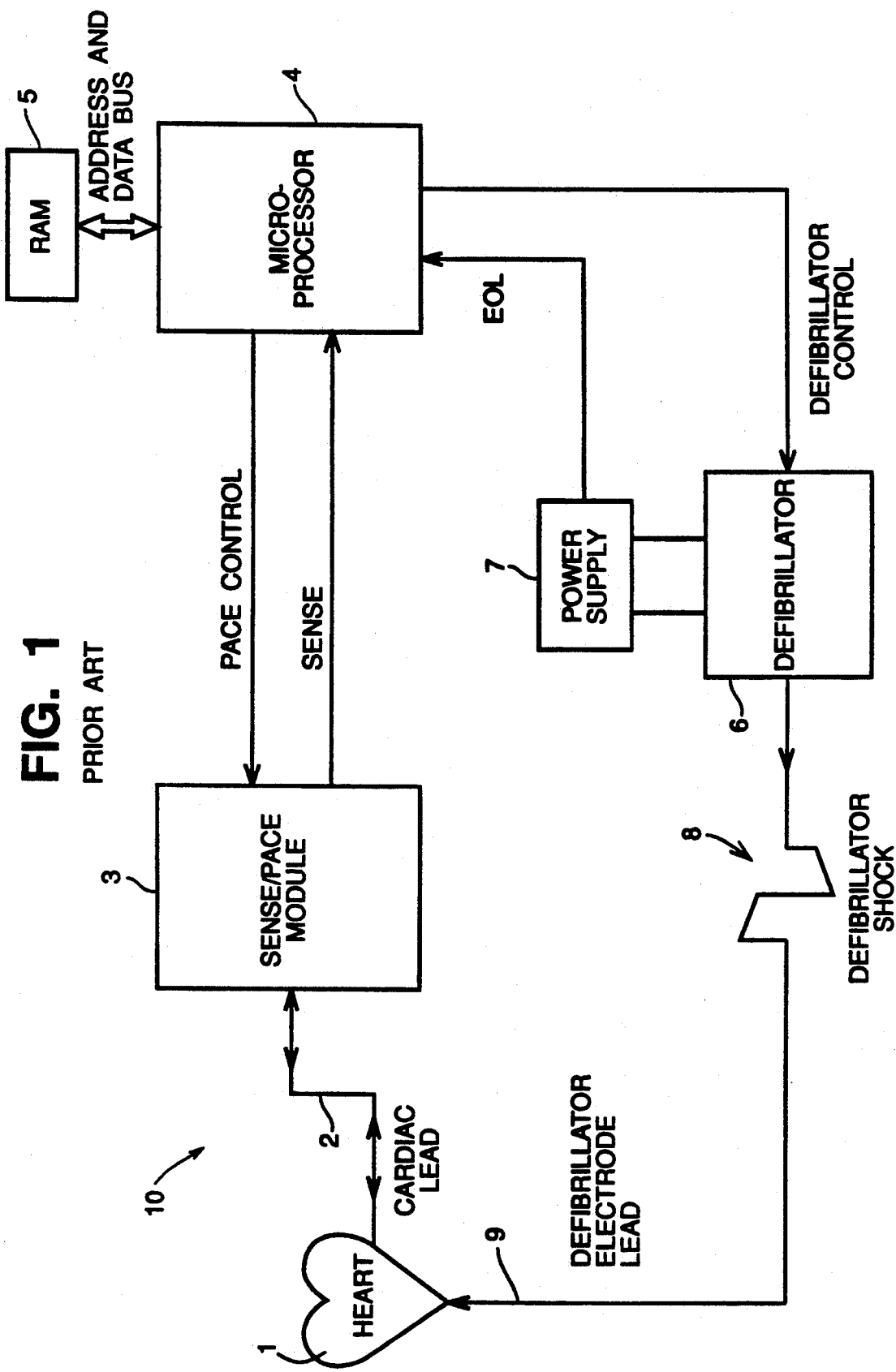
FIG. 1 depicts a block diagram of a conventional implantable microprocessor-controlled cardioverter/-defibrillator which utilizes sensing at one site within the ventricles.

Referring to FIG. 1, there is depicted a block diagram of a conventioanl microprocessor-controlled, implantable cardioverter/defibrillator (ICD) 10 which comprises: a cardiac lead 2 connected to the patient's heart 1; a sense/pace module 3 for the detection of analog signals representing the cardiac electrical activity and for the delivery of pacing pulses to the heart; a microprocessor 4 which responds to various inputs from the pace/sense module 3 and a defibrillator module 6, so as to generate various control and data outputs to both the sense/pace module 3 and the defibrillator module 6; a RAM 5 which acts as a scratch pad memory during execution of the various programs used by microprocessor 4; a power supply 7; an end-of-life signal line EOL for providing to microprocessor 4 a logic signal indicative of the approach of battery failure in power supply 7; and a defibrillator electrode lead 9 for transfer-ring the energy of a defibrillation shock 8 from the ICD implant 10 to the heart muscle.

Figure 2:
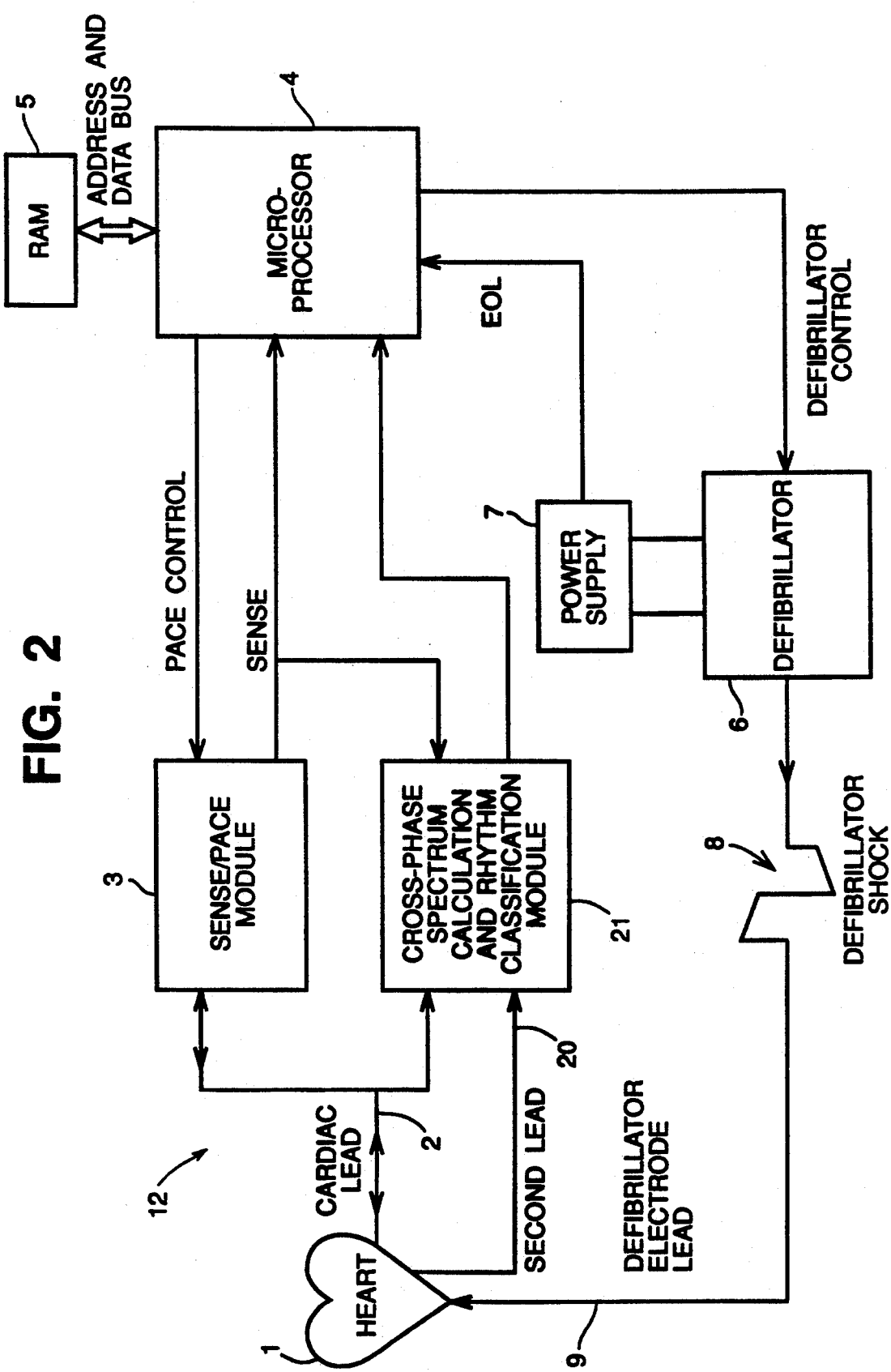
FIG. 2 depicts a block diagram of an implantable cardioverter/defibrillator, in accordance with the present invention, which utilizes sensing at two sites within the ventricles, and includes a module for cross-phase spectrum calculation and rhythm classification.

Referring to FIG. 2, there is depicted a block diagram of an ICD 12, in accordance with the present invention, that incorporates a cross-phase spectrum calculation and rhythm classification module 21. There is also provided a second cardiac lead 20, including separate sensing electrodes (not shown), which provides a second cardiac signal for input to the cross-phase spectrum calculation and rhythm classification module. The cross-phase spectrum calculation and rhythm classification module feeds extra information to the microprocessor 4 so that it may better respond to the state of the heart.

In operation the sense/pace module 3 detects analog signals from the heart 1 and converts the detected signals into digital signals. These digital signals denote a depolarization of the heart 1. These digital signals are passed both to the microprocessor 4 and to the cross-phase spectrum calculation and rhythm classification module 21.

Referring to FIG. 3, there is depicted a block diagram of the cross-phase spectrum calculation and rhythm classification module 21 of FIG. 2, which module comprises a Fast Fourier Transformer 31, an averager 33, and a comparator 32. The output of the comparator 32 is passed to the microprocessor 4 of FIG. 2.

The cross-phase spectrum calculation and rhythm classification module 21 receives as input the analog signals from the two cardiac sensing leads 2 and 20. These are applied to the Fast Fourier Transformer 31.

The Fast Fourier Transformer 31 calculates spectra for each of the input waveforms, then calculates the cross-phase spectra from these two spectra. This cross-phase spectrum is then passed to both the averager 33 and the comparator 32.

The averager 33 collects the cross-phase spectrum information for a number of successive heart beats, and calculates a representative or average cross-phase spectrum. This average cross-phase spectrum is passed to the comparator 32.

The comparator 32 has as inputs the cross-phase spectrum for the current heart beat, from the Fast Fourier Transformer 31, and also the average cross-phase spectrum from the averager 33. It compares the two, and if they are similar it concludes that the current heart beat was a normal one (presumably physiological in origin). If on the other hand the current cross-phase spectrum was dissimilar to the average cross-phase spectrum, the comparator concludes that the current heart beat was abnormal (of pathological origin). This classification of physiological or pathological is passed on to the microprocessor 4 of FIG. 2.

The microprocessor 4 uses the heart beat classification from the comparator 32 to diagnose the state of the heart. A number of successive pathological heart beats indicate that the heart is in an a pathological rhythm, and appropriate conventional pacing or shock therapy is initiated by the microprocessor. The calculation and analysis of the cross-phase spectrum is depicted in FIGS. 4A to 7.

Figure 4A:
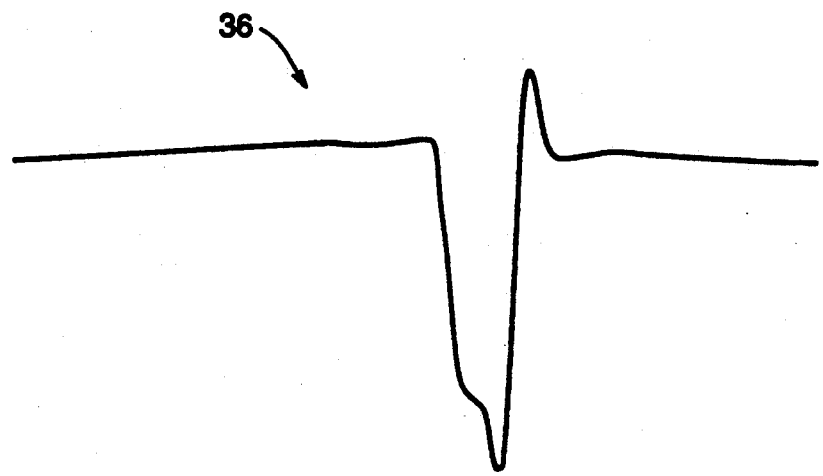
FIGS. 4A and 4B depict the input signals from the two ventricular sites which are used for calculation of the cross-phase spectrum. The mean has been removed, and each has been multiplied by a Hanning window. These are normal steps in the calculation of the Fast Fourier Transform (see, e.g., Bergland, G. D., "A Guided Tour of the Fast Fourier Transform," IEEE Spectrum, Vol. 6, pp. 41–52, July 1969)
Figure 4B:
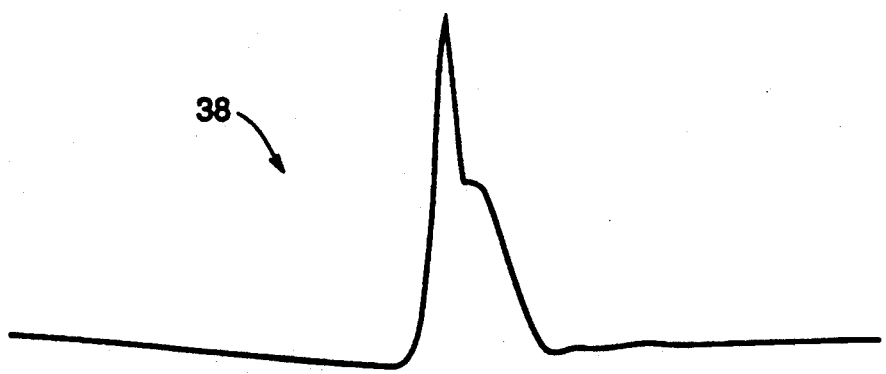

FIGS. 4A and 4B show two analog signals 36 and 38 derived from sites in the heart 1 via the two sensing lead systems 2 and 20, respectively. (See FIGS. 12A-12D for examples of site locations for the electrode pairs). Each of these signals are mean-removed. This is a mathematical technique that ensures that the signal has an average of zero. The signals have also been windowed using a Hanning window. This is a process which reduces the signal amplitude at the ends of the segment of the signal. Both these processes are necessary precursors to the application of the Fast Fourier Transform process. (See, e.g., Oppenheim, A. V., and Schafer, R. W., "Digital Signal Processing", Prentice-Hall, 1975, and Nussbaumer, H. J., "Fast Fourier Transform and Convolution Algorithms", 2nd ed., Springer Verlag, Berlin, 1982.)

Figure 5A:
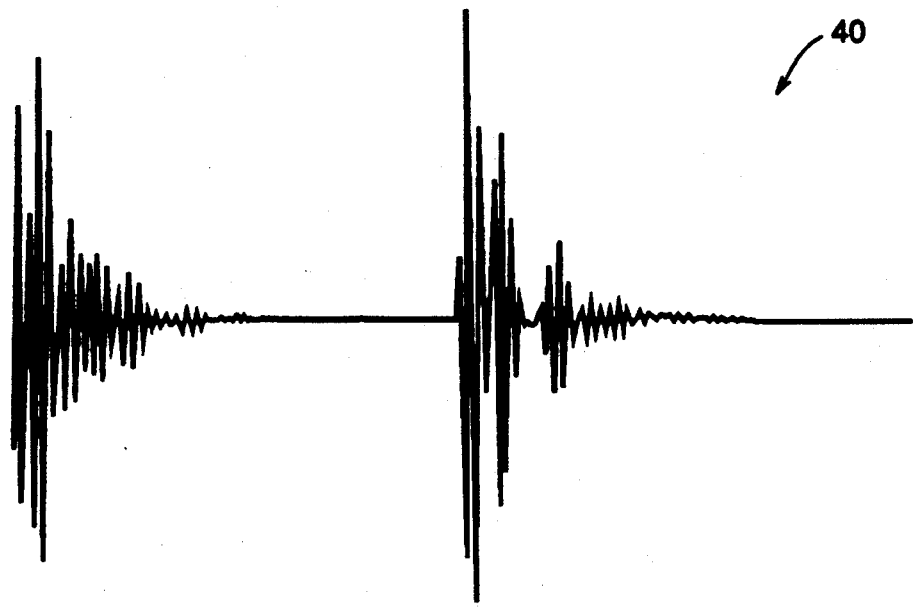
FIGS. 5A and 5B depict the spectra derived by application of the Fast Fourier Transform (FFT) to the signals of FIGS. 4A and 4B.
Figure 5B:

FIGS. 5A and 5B show two spectra 40 and 42 generated by application of the Fast Fourier Transform to each of the mean-removed and windowed signals of FIGS. 4A and 4B, respectively. The spectra show the distribution of energy at different frequency bands within the signal.

Figure 6:
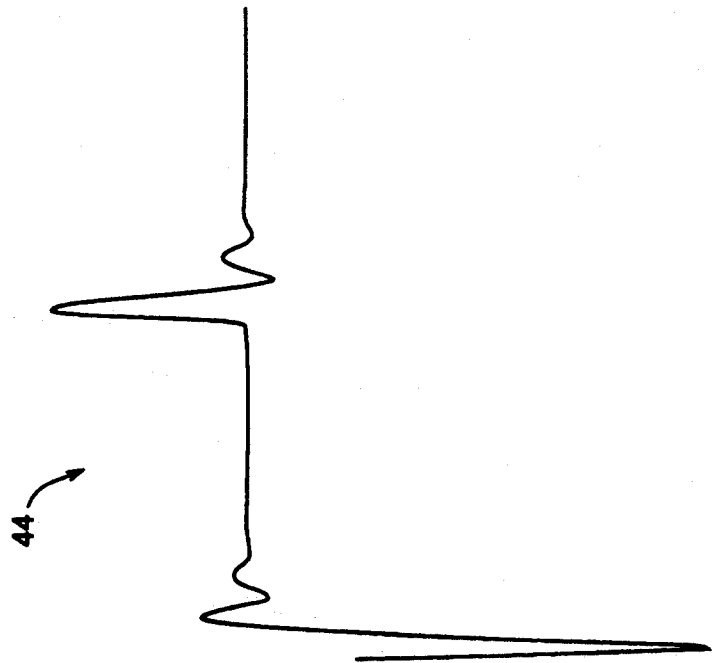
FIG. 6 depicts the cross-spectrum derived as the complex conjugate product of the two spectra of FIGS. 5A and 5B.

FIG. 6 show the cross-spectrum 44 (real and imaginary) which is calculated by forming the complex-conjugate product of the two individual Fast Fourier Transform spectra of FIG. 5. It is this step which is the crucial one in combining the information from the two different signals.

Figure 7:
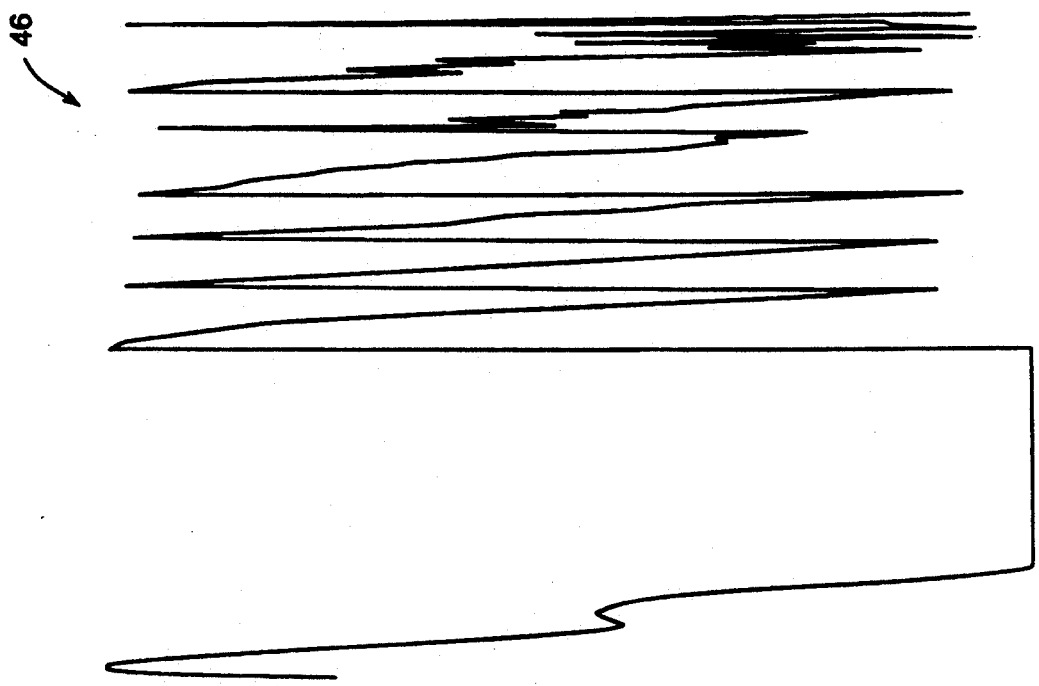
FIG. 7 depicts the cross-spectrum in log-magnitude and phase representation, derived by application of a rectangular-to-polar conversion on the cross-spectrum of FIG. 6.

FIG. 7 shows the cross-spectrum 46 in log-magnitude and phase representation, calculated by the application of rectangular-to-polar transformation to the cross-spectrum 44 of FIG. 6.

Figure 8:
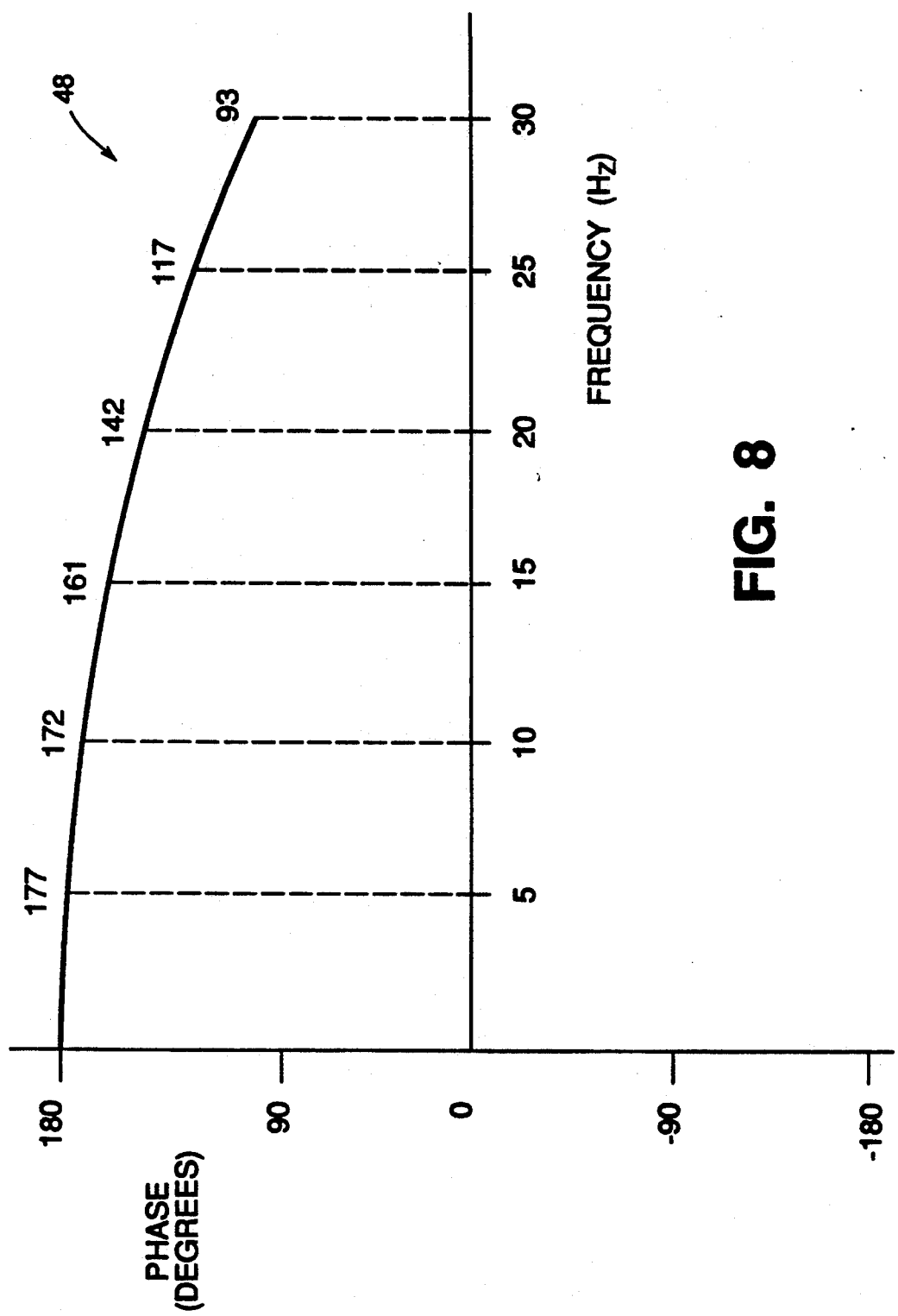
FIG. 8 depicts the process of sampling the cross-phase spectrum at 5 Hz intervals.

FIG. 8 shows the process of sampling the phase part 48 of the cross-spectrum at particular frequencies. These frequencies are ideally at 5 Hz increments from 5 to 30 Hz. These sampled values are the cross-phase spectrum values.

Figure 9:
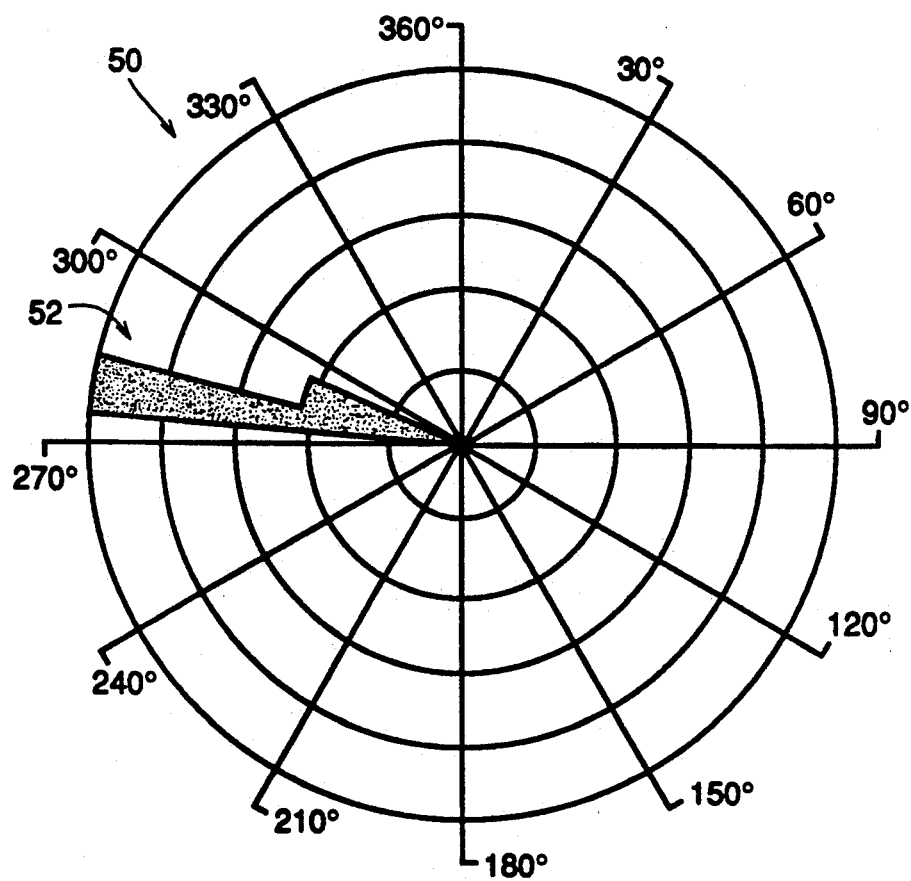
FIG. 9 depicts the sample distribution of the cross-phase spectrum at 15 Hz for a large number of heart beats from a patient in normal sinus rhythm (NSR)

FIG. 9 shows a circular histogram 50 which displays the distribution of cross-phase spectrum values 52 over a large number of heart beats of the physiological rhythm, in this case normal sinus rhythm (NSR), at a particular frequency (in this case 15 Hz for 219 electrograms from a patient in normal sinus rhythm). These histograms can be generated for each of the frequencies in the range of analysis, ideally 5 to 30 Hz in 5 Hz steps.

Figure 10:
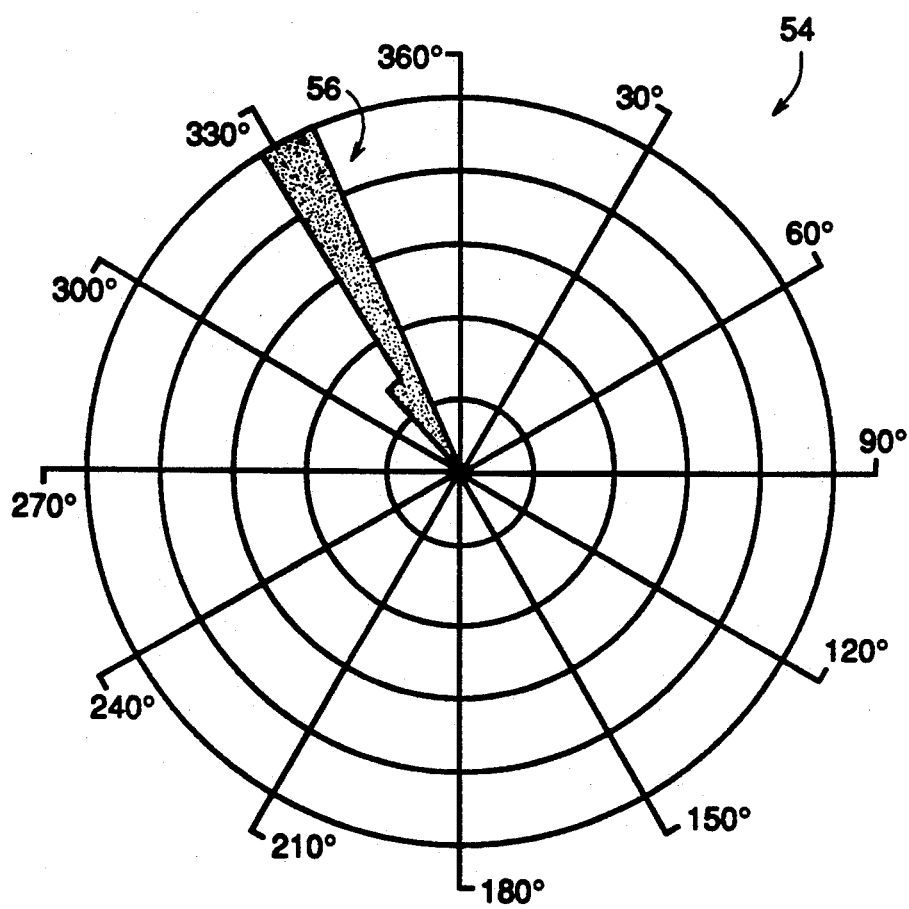
FIG. 10 depicts the sample distribution of the cross-phase spectrum at 15 Hz for a large number of heart beats from the same patient as FIG. 9, this time in ventricular tachycardia (VT)

FIG. 10 shows a histogram 54 for the same patient and the same frequency, for 65 heart beats, this time in the pathological rhythm ventricular tachycardia (VT). Since the histograms of observed values for normal sinus rhythm (52 of FIG. 9) and ventricular tachycardia (56 of FIG. 10) do not overlap, it is possible to determine if the heart-beat was physiological or pathological. Note that the distribution 56 of FIG. 10 is clearly different from the distribution 52 shown in FIG. 9. Pathological rhythms other than VT result in histograms that differ from those shown in FIGS. 9 and 10 and from each other.

Figure 11A:
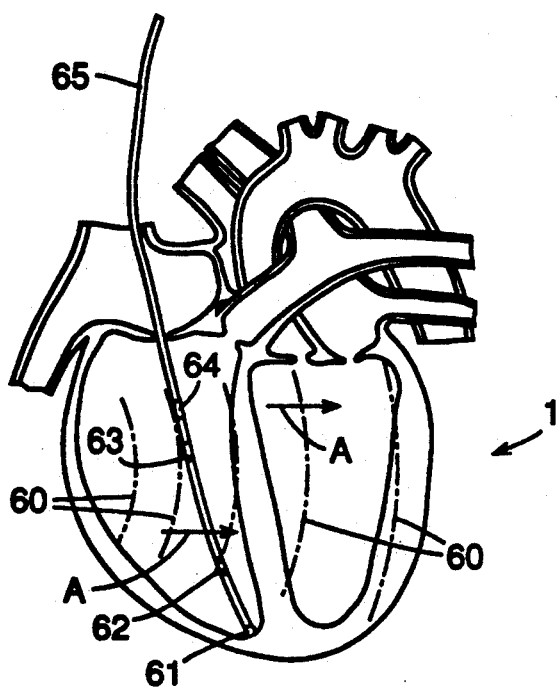
FIGS. 11A and 11B depict respective normal and abnormal flows of depolarization in the heart, corresponding to physiological and pathological rhythms, respectively, and show the different depolarization arrival times that will occur at the electrodes for differing rhythms.
Figure 11B:
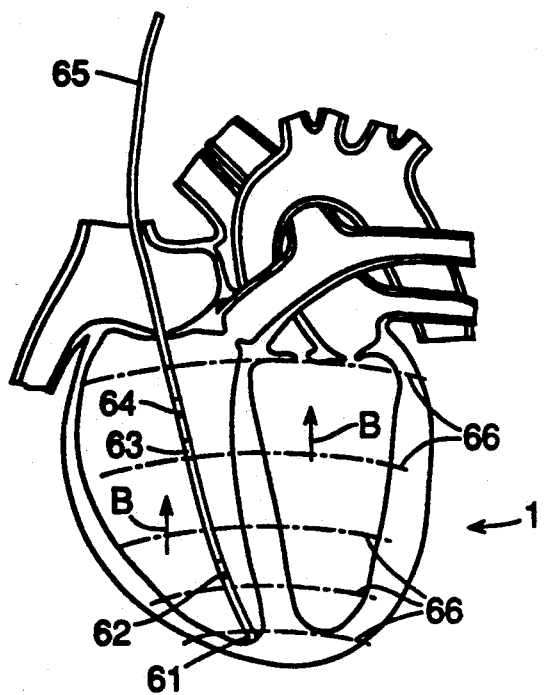

FIGS. 11A and 11B depict propagations of depolarl-,zation wavefronts in two different rhythms, showing differing arrival times at two electrode pairs. It shows the mode by which the proposed technique is able to distinguish between physiological and pathological heart beats. In FIG. 11A, a wave of depolarization 60 is flowing through the heart, in the direction of arrows A, almost parallel to the axis between the two electrode pairs 61, 62 and 63, 64. The wavefront arrives at the two electrode pairs at almost the same time, so there is only a slight delay between the electrical signals. In FIG. 11B, the wave of depolarization 66, moving in the direction of arrows B, is almost perpendicular to the axis between the electrode pairs 61, 62 and 63, 64. Thus the wave of depolarization 66 in this case first crosses one electrode pair 61, 62, and later crosses the other pair 63, 64. There is significant delay between the electrical activity observed on the two electrode pairs.

The use of the cross-phase spectrum provides a sensitive technique for observing the different conduction directions that occur in physiological and pathological activation of the ventricles. It provides a much more robust technique than simply measuring the time delay between the two electrode pairs, because it is insensitive to changes in the electrogram morphology observed at the two locations.

Figure 12A:
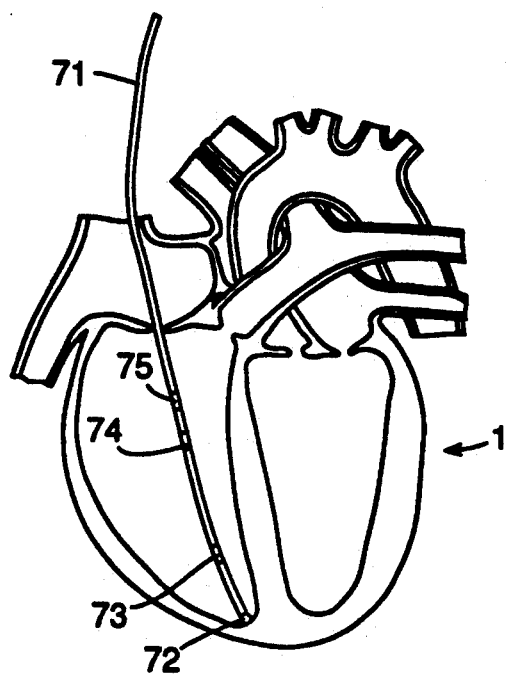
FIGS. 12A, 12B, 12C and 12D depict a number of possible lead and electrode configurations that may be used in the invention.
Figure 12B:
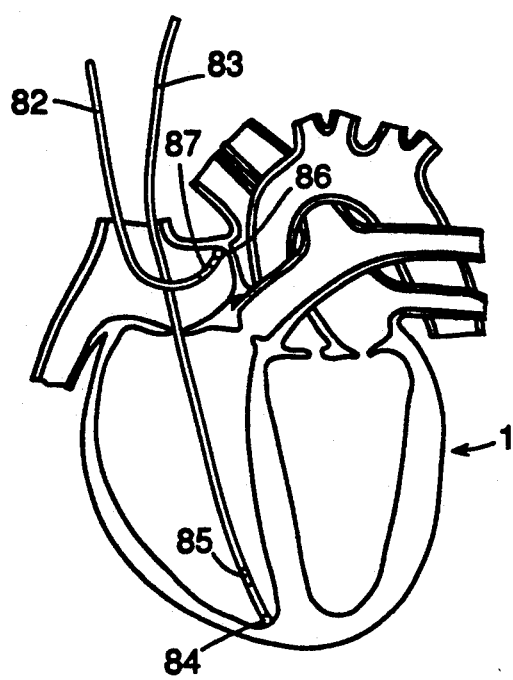
Figure 12C:
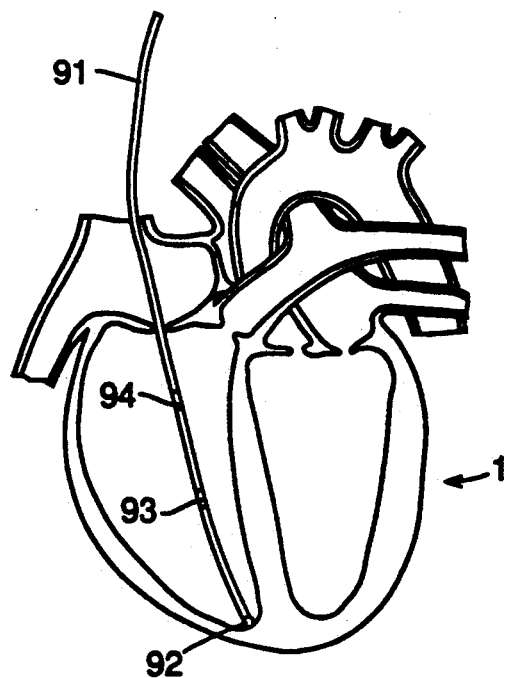
Figure 12D:
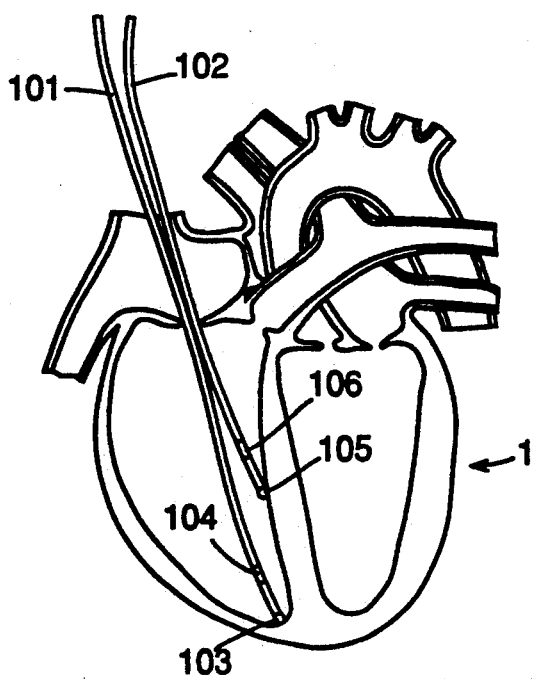

FIGS. 12A, 12B, 12C and 12D show a number of possible alternative lead configurations. In FIG. 12A, there is shown a single lead 71 with four electrodes, 72, 73 and 74, 75, forming the required two electrode pairs 72, 73 and 74, 75. In FIG. 12B, there are two leads, a first lead 82 in the atrium, and a second lead 83 in the ventricle. Lead 82 includes an electrode pair 84, 85, and lead 83 includes an electrode pair 86, 87. Thus each lead provides one of the two required electrode pairs. In FIG. 12C, a single lead 91 is provided with three electrodes 92, 93 and 94. The middle electrode 93 is used in conjunction with the upper electrode 94 to provide one electrode pair, and in conjunction with the lower electrode 92 to provide the other required electrode pair. Finally in FIG. 12D, two ventricular leads 101 and 102 are provided. Lead 101 includes an electrode pair 103, 104, and lead 102 includes an electrode pair 105, 106.

It will be apparent from the foregoing description that the present invention provides an improved implantable cardioverter/defibrillator and method which employs cross-phase spectrum analysis for arrhythmia detection. It facilitates reliable differentiation between tachycardias having a physiological origin and tachycardias having a pathological origin, even when the possible ranges of heart rates for the two types of tachycardia have a degree of overlap. The discrimination between the two types of tachycardias is, moreover, unaffected by normal changes in electrogram morphology. In addition, in the same way as has been described above different types of pathological tachyarrhythmias may be sub-classified by the invention by comparing them against previously recorded cross-phase spectrums of different types of pathological tachyarrhythmias allowing more appropriate selection of therapy modalities.

While there have been shown and described what are presently considered to be the preferred embodiments of this invention, it will be obvious to those skilled in the art that various changes and modifications may be made without departing from the broader aspects of the invention. For example, this invention is applicable whether the cross-phase spectrum is calculated via Fast Fourier Transform or via other well known means, including analog delay lines. The invention is also applicable to detecting other changes in the heart such as ischemia or infarction. Moreover, the reference cross spectrum may be calculated using mean, median, confidence interval, or other suitable well known means. Furthermore, the electrodes may be positioned anywhere within the heart, or outside the heart, or anywhere in or on the body, and may apply to 3, 4, cr several electrodes. It is, therefore, aimed in the appended claims to cover all such changes as fall within the true spirit and scope of this invention.

What is claimed is:

1. A method of detecting and reverting pathological heart rhythms of a patient, comprising the steps of:
   sensing each of a plurality of electrical heart rhythm signals of the patient at two different locations;
   calculating cross-phase spectra of sensed heart rhythm signals;
   classifying the heart rhythms based upon information contained in said cross-phase spectra; and,
   delivering appropriate therapy to the patient's heart to revert heart rhythms classified as pathological.

2. A method according to claim 1, wherein said sensing step includes the sub-step of sensing electrical heart rhythm signals at two different locations within the heart.

3. A method according to claim 2, wherein said therapy delivering step includes the sub-step of delivering anti-tachycardia pacing therapy to the heart to revert pathological ventricular tachycardia.

4. A method according to claim 2, wherein said therapy deliverying step includes the sub-step of delivering defibrillation shock therapy to the heart to revert ventricular fibrillation.

5. Apparatus for detecting and reverting pathological heart rhythms of a patient, comprising:
   means for sensing each of a plurality of electrical heart rhythm signals of the patient at two different locations;
   means for calculating cross-phase spectra of the sensed heart rhythm signals;
   means for classifying heart rhythms based upon information contained in said cross-phase spectra; and,
   means for delivering appropriate therapy to the patient's heart to revert heart rhythms classified as pathological.

6. Apparatus according to claim 5, wherein said sensing means senses said heart rhythm signals at two different locations within the heart.

7. Apparatus according to claim 6, wherein said therapy delivering means delivers anti-tachycardia pacing therapy to the heart to revert pathological ventricular tachycardia.

8. Apparatus according to claim 6, wherein said therapy delivering means delivers defibrillation shock therapy to the heart to revert ventricular fibrillation.

9. Apparatus according to any one of claims 6–8, wherein said sensing means includes at least 2 pairs of bipolar sensing electrodes, each of said pairs of sensing electrodes serving to sense each of said heart rhythm signals at one of said two locations within the heart.

10. Apparatus according to claim 9, wherein said apparatus further includes an endocardial lead, and wherein said two pairs of bipolar sensing electrodes include three electrodes positioned at spaced apart locations on a distal portion of said endocardial lead, one of said three electrodes serving as a common electrode for both of said two pairs of bipolar sensing electrodes.

11. Apparatus according to claim 9, wherein said apparatus further includes two endocardial leads, and wherein each of said two pairs of bipolar sensing electrodes includes two electrodes positioned on a distal portion of a corresponding one of said endocardial leads which is other than the endocardial lead that carries the two electrodes of the other of said two pairs of bipolar sensing electrodes.

12. Apparatus according to any one of claims 6–8, wherein said calculating means includes means for selectively performing Fast Fourier Transforms of the heart rhythm signals that are sensed for each heartbeat at said two locations within the heart.

13. Apparatus according to claim 12, wherein said classifying means includes averaging means for calculating an average cross-phase spectrum over a number of successive heart beats, and comparator means for comparing a cross-phase spectrum from a current heartbeat with said average cross-phase spectrum to determine whether said current heartbeat is a normal heartbeat or an abnormal heartbeat.

14. Apparatus according to claim 13, wherein said classifying means includes means for generating signals corresponding to physiological and pathological heartbeats, and further including microprocessor means responsive to said signals generated by said classifying means and coupled to said therapy delivering means for actuating said therapy delivering means ot deliver said therapy to the patient's heart upon receiving signals from said classifying means that correspond to pathological heartbeats.

15. Apparatus according to claim 14, wherein said sensing means includes at least 2 pairs of bipolar sensing electrodes, each of said pairs of sensing electrodes serving to sense each of said heart rhythm signals at one fo said two locations within the heart.

16. Apparatus according to claim 15, wherein said apparatus further includes an endocardial lead, and wherein said two paris of bipolar sensing electrodes include three electrodes positioned at spaced apart locations on a distal portion of said endocardial lead, one of said three electrodes serving as a common electrode for both of said two pairs of bipolar sensing electrodes.

17. Apparatus according to cliam 15, wherein said apparatus includes two endocardial leads, and wherein each of said two paris of bipolar sensing electrodes includes two electrodes positioned on a distal portion of a corresponding one of said endocardial leads which is other than the endocardial lead that carries the two electrodes of the other of said two pairs of bipolar sensing electrodes.

* * * * *